US012154688B2

United States Patent
Trovato et al.

(10) Patent No.: US 12,154,688 B2
(45) Date of Patent: Nov. 26, 2024

(54) SYSTEMS AND METHODS FOR GENERATING CORRECT RADIOLOGICAL RECOMMENDATIONS

(71) Applicant: KONINKLIJKE PHILIPS N.V., Eindhoven (NL)

(72) Inventors: Karen Irene Trovato, Putnam Valley, NY (US); Yuechen Qian, Lexington, MA (US); Gabriel Ryan Mankovich, Boston, MA (US); Lucas De Melo Oliveira, Melrose, MA (US); Ranjith Naveen Tellis, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 600 days.

(21) Appl. No.: 15/767,240

(22) PCT Filed: Oct. 7, 2016

(86) PCT No.: PCT/IB2016/056005
§ 371 (c)(1),
(2) Date: Apr. 10, 2018

(87) PCT Pub. No.: WO2017/064600
PCT Pub. Date: Apr. 20, 2017

(65) Prior Publication Data
US 2019/0074074 A1  Mar. 7, 2019

Related U.S. Application Data

(60) Provisional application No. 62/241,238, filed on Oct. 14, 2015.

(51) Int. Cl.
G16H 50/20 (2018.01)
G06T 7/00 (2017.01)
(Continued)

(52) U.S. Cl.
CPC .......... *G16H 50/20* (2018.01); *G06T 7/0012* (2013.01); *G16H 15/00* (2018.01); *G16H 30/40* (2018.01); *G16H 30/20* (2018.01); *G16H 70/20* (2018.01)

(58) Field of Classification Search
CPC ........ G16H 50/20; G16H 15/00; G16H 30/40; G16H 30/20; G16H 70/20
See application file for complete search history.

(56) References Cited

U.S. PATENT DOCUMENTS 9,146,663 B2 *  9/2015  Kreeger .................. A61B 6/502
10,162,483 B1 * 12/2018  Fram ..................... G06F 3/0482
(Continued)

FOREIGN PATENT DOCUMENTS

WO   WO-2015031296 A1 *  3/2015  ............. G16H 30/20
WO        2015114485 A1      8/2015

OTHER PUBLICATIONS

Ronald L. Eisenberg, "Compliance with Fleischner Society Guidelines of Small Lung Nodules: A Survey of 834 Radiologists", Apr. 2010, pp. 218-224 (Year: 2010).*

*Primary Examiner* — Rajesh Khattar
*Assistant Examiner* — Steven G. S. Sanghera

(57) ABSTRACT

A system and method for generating a radiological report. The system and method displaying, on a display, an image of a region of interest, determining an image characteristic of the region of interest, determining, via a processor, a recommendation based on the image characteristic, and generating, via the processor, a report including the recommendation.

22 Claims, 4 Drawing Sheets

(51) Int. Cl.
 G16H 15/00 (2018.01)
 G16H 30/20 (2018.01)
 G16H 30/40 (2018.01)
 G16H 70/20 (2018.01)

(56) References Cited

U.S. PATENT DOCUMENTS

| | | |
|---|---|---|
| 2002/0131625 A1 | 9/2002 | Vining |
| 2009/0080734 A1 | 3/2009 | Moriya et al. |
| 2011/0109650 A1 | 5/2011 | Kreeger |
| 2011/0125680 A1* | 5/2011 | Bosworth .............. G16H 50/20 706/54 |
| 2012/0143623 A1 | 6/2012 | Opfer |
| 2014/0219500 A1 | 8/2014 | Moehrle et al. |
| 2014/0365232 A1* | 12/2014 | Sadeghi ................ G16H 50/20 705/2 |

* cited by examiner

SYSTEMS AND METHODS FOR GENERATING CORRECT RADIOLOGICAL RECOMMENDATIONS

CROSS-REFERENCE TO PRIOR APPLICATIONS

This application is the U.S. National Phase application under 35 U.S.C. § 371 of International Application Serial No. PCT/IB2016/056005, filed on Oct. 7, 2016, which claims the benefit of U.S. Patent Application No. 62/241,238, filed on Oct. 14, 2015. This application is hereby incorporated by reference herein.

BACKGROUND

Various medical imaging modalities are routinely used in medicine. For example, doctors frequently use X-ray, ultrasound, computed tomography (CT), and magnetic resonance imaging (MRI) to image and diagnose patients. These medical images are typically read by radiologists. Although many images are complex and require intense attention to detail, radiologists are under increasing pressure to be efficient. For example, many radiologists may only spend 1-2 minutes reading an image or set of images. Based on the reading, a radiologist dictates or types a report including the key findings (assessment of normal or abnormal anatomy) and may: (1) diagnose disease and provide disease status; or may (2) provide a recommendation for follow-up/next steps.

Recommendations provided by radiologists often include further imaging studies. For example, a radiologist may recommend further imaging with a different modality to improve the understanding of the disease by imaging with a different modality. Alternatively, a radiologist may recommend further imaging to detect changes in the disease that may occur over time. If these follow up imaging procedures are not performed, the window during which the disease can be successfully treated may be missed, which may result in patient fatality or more expensive treatment. For example, if a small lesion is detected on an image, a common approach may be to take another image within a certain timeframe to observe the growth and progression of the lesion. If the imaging is performed too late (or never), the time to treat the lesion when it is small and curable may have been missed. Despite the importance of performing the follow up recommendations of radiologists, many radiologist recommendations lack the specificity needed for the recommendations to be effective. For example, many recommendations omit the specific modality for the follow-up imaging and/or a timeframe within which the imaging should be performed. Without such specific information, the radiologist's recommendation may be overlooked, misinterpreted, and/or never acted upon.

SUMMARY

A method for generating a radiological report. The method including displaying, on a display, an image of a region of interest, determining an image characteristic of the region of interest, determining, via a processor, a recommendation based on the image characteristic, and generating, via the processor, a report including the recommendation.

A system for generating a radiological report. The system comprising a display displaying an image including a region of interest and a processor determining an image characteristic of the region of interest, determining a recommendation based on the image characteristic and generating a report including the recommendation.

A non-transitory computer-readable storage medium including a set of instructions executable by a processor. The set of instructions, when executed by the processor, causing the processor to perform operations, comprising displaying an image of a region of interest, determining an image characteristic of the region of interest, determining a recommendation based on the image characteristic, and generating a report including the recommendation.

BRIEF DESCRIPTION

DETAILED DESCRIPTION

Figure 1:
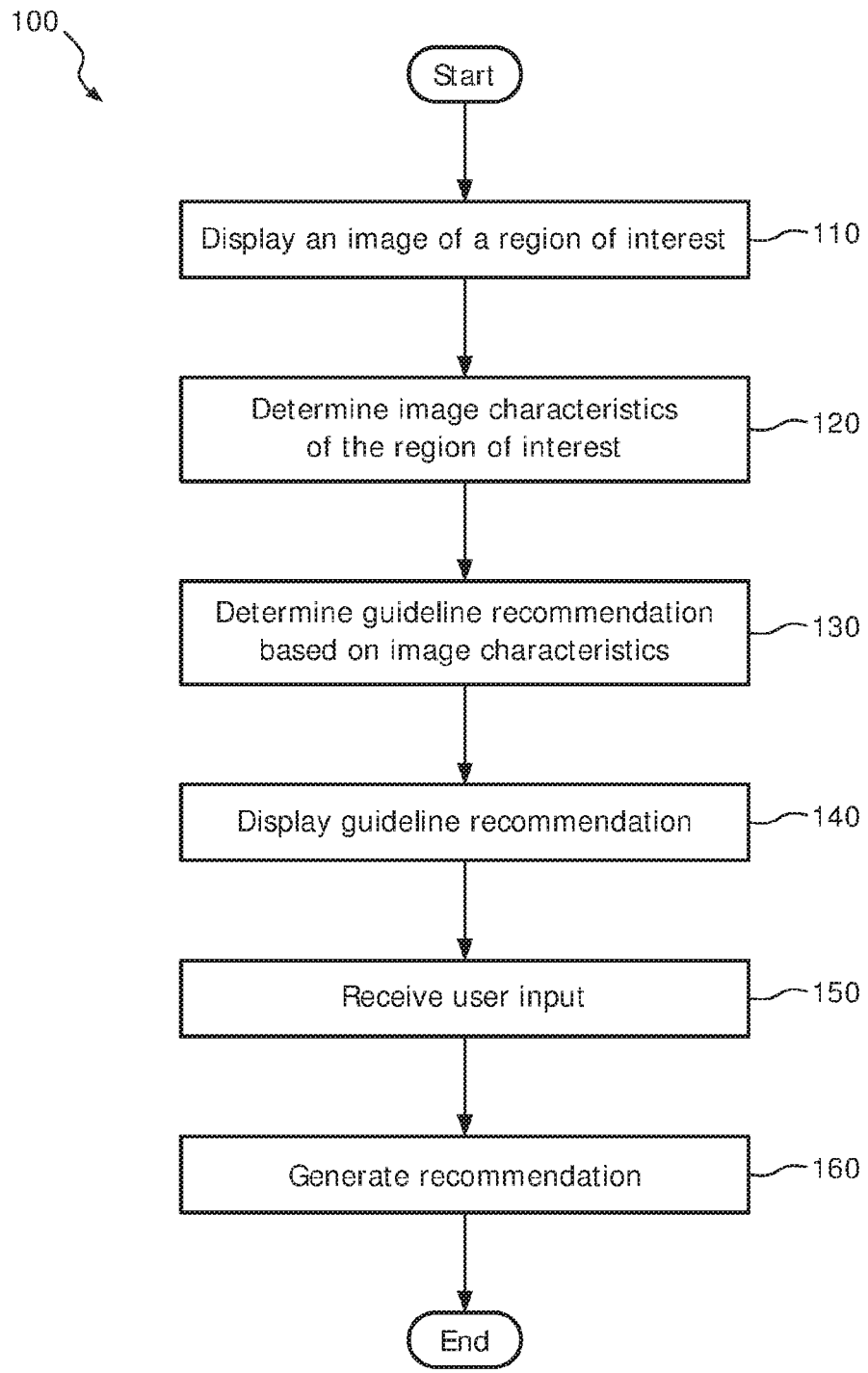
FIG. 1 is a flow diagram of an exemplary method according to an exemplary embodiment.

The exemplary embodiments may be further understood with reference to the following description and the appended drawings, wherein like elements are referred to with the same reference numerals. The exemplary embodiments relate to a system and method for generating medical recommendations. In particular, the exemplary embodiments describe a system and method for generating a radiological recommendation from an image. Certain exemplary embodiments of the present disclosure provide a recommendation generation mechanism integrated into existing workflows to facilitate generation of fully-formed radiological recommendations. An aspect of the present disclosure provides automatic determination of guideline recommendations based on certain characteristics of the image. Other aspects of the present disclosure provide user input mechanisms in the generation of the recommendations. Although the exemplary embodiments are specifically described with respect to radiologists and specific lesions and anatomies, it will be understood by those of skill in the art that the system and method of the present disclosure may be used by other health professionals for patients having any of a variety of diseases or conditions.

FIG. 1 shows an exemplary method 100 according to an exemplary embodiment of the present disclosure. As shown in FIG. 1, in a step 110, a region of interest from an image is displayed to be read by a user (e.g., a radiologist). The region of interest may include a lesion, a polyp, a tumor, a nodule, or any other feature, and the anatomy may include a lung, a brain, or any other organ or anatomy of a patient that may be of interest.

In a step 120, one or more image characteristics of the region of the region of interest are determined. Image characteristics may include a size, shape/texture, distribution/uniformity, etc. of the region of interest. For example, a characteristic may include a maximum measure of cross-section or 3D volume of an anatomy, lesion, nodule, or tumor. Shape/texture can be described as, for example, speculated (spikey)/lobulated (rounded), or symmetric/asymmetric. Distribution or uniformity can indicate may indicate a focal or diffuse region of interest and/or a heterogeneous or homogeneous disease. Currently, the size is the most frequently used characteristic used for incidentally detected lesions (lung nodule, adrenal mass). In addition, other patient characteristics may also be used. For example, a history of smoking or heavy exposure to asbestos are both indicators for high risk of lung cancer. Image characteristics may be manually generated (e.g., input by a radiologist, measurement taken by a radiologist, etc.), or may be automatically generated using image processing or other techniques.

In a step 130, recommendations are determined based on the determined image characteristics and the accepted guideline. According to an exemplary embodiment, the radiologist may augment the image (e.g., take a measurement), which may trigger an automatic determination of the recommendations. The radiologist may also indicate the finding (such as lung nodule) through the user interface. Alternatively, the radiologist can perform this in the reverse order: identify the region as a lung nodule and then take a measurement. For example, a radiologist reading an image may identify a lung nodule and perform a measurement as 7 mm, which may trigger an automatic determination of an accepted guideline for incidental lung nodule findings such as, for example, the Fleischner Guidelines, based on the given size of the nodule. It will be understood by those of skill in the art, however, that various guidelines, depending on, for example, the anatomy of the region of interest may be triggered to determine the guideline recommendations. The guideline recommendation may include, for example, a modality and a timeframe in which the follow-up should be completed.

According to another example guideline which may be triggered when, for example, an incidentally detected adrenal mass is detected on a CT or ultrasound, recommendations may be based on the greatest diameter of the lesion or mass. For example, if the mass has a diameter of less than 3 cm, the patient has no signs or symptoms and the screening lab tests normal, then radiographic surveillance at 3 months and then every 5 months for 2 years may be recommended. If however, the screening lab tests are not normal, recommendations may be based on the symptoms. When the mass is measured to be, for example, between 3 and 6 cm, an MRI and endocrine evaluation may be recommended. Masses greater than or equal to 6 cm may result in a recommendation for a surgical referral.

In a step 140, the guideline recommendations may be displayed to the radiologist. For example, for the measurement of a 7 mm lung nodule, the guideline recommendations for a low-risk patient and a high-risk patient having a 6-8 mm nodule may be displayed. Based upon the Fleischner Guideline, the recommendation may be displayed as "A follow-up CT scan should be performed within 6-12 months in a non-smoker, or in 3-6 months if the patient is a smoker (high risk)." If the patient risk factor is unknown, then both statements may be generated so that the information is passed back to the referring physician for the appropriate course. If the patient risk factor is known, then the appropriate, specific recommendation can be generated.

Upon display of the guideline recommendations, the radiologist may select the appropriate recommendation in a step 150. Alternatively, the step 150 may also include other inputs that the radiologist may make. For example, the radiologist may reject and/or customize the guideline recommendation in view of other factors known to the radiologist (e.g., patient history, etc.). For example, where the above exemplary recommendation is displayed, the radiologist may input whether or not the patient is a smoker, if known, to customize the recommendation to the specific patient. Step 150, however, may be optional in other exemplary embodiments since some guideline recommendations may only include a single recommendation.

In a step 160, a recommendation, which includes at least the timeframe within which follow-up imaging should be performed and the imaging modality to be used, is generated. In one exemplary embodiment, the recommendation may be included in a standard radiology report, which is generated while or after the radiologist has read the images. A standard radiological report may include, for example, patient demographics (patient information such as name, gender, medical number, date of birth, etc.), clinical indication (e.g., health history and rationale for the exam, body of report (e.g., describing findings of the image), and impressions (e.g., a summary section where diagnosis and recommendations for follow-up). The recommendation in a report generated in the step 160 is often included in the impressions or findings section of a standard radiology report. The recommendation within the report may take any form, and may include any text, graphics, audio, or any other indicators of the contents of the report, which may be provided to the patient or other medical professionals. Current reports, however, are primarily text. It may be preferable to include a cross-reference to a measurement made by the radiologist on which the recommendation is made. This may include, for example, the image slice number and X-Y locations of the end points of the lesion on the image slice. Further, the recommendation within the report may be transmitted electronically, or may be printed, or displayed.

Figure 2:
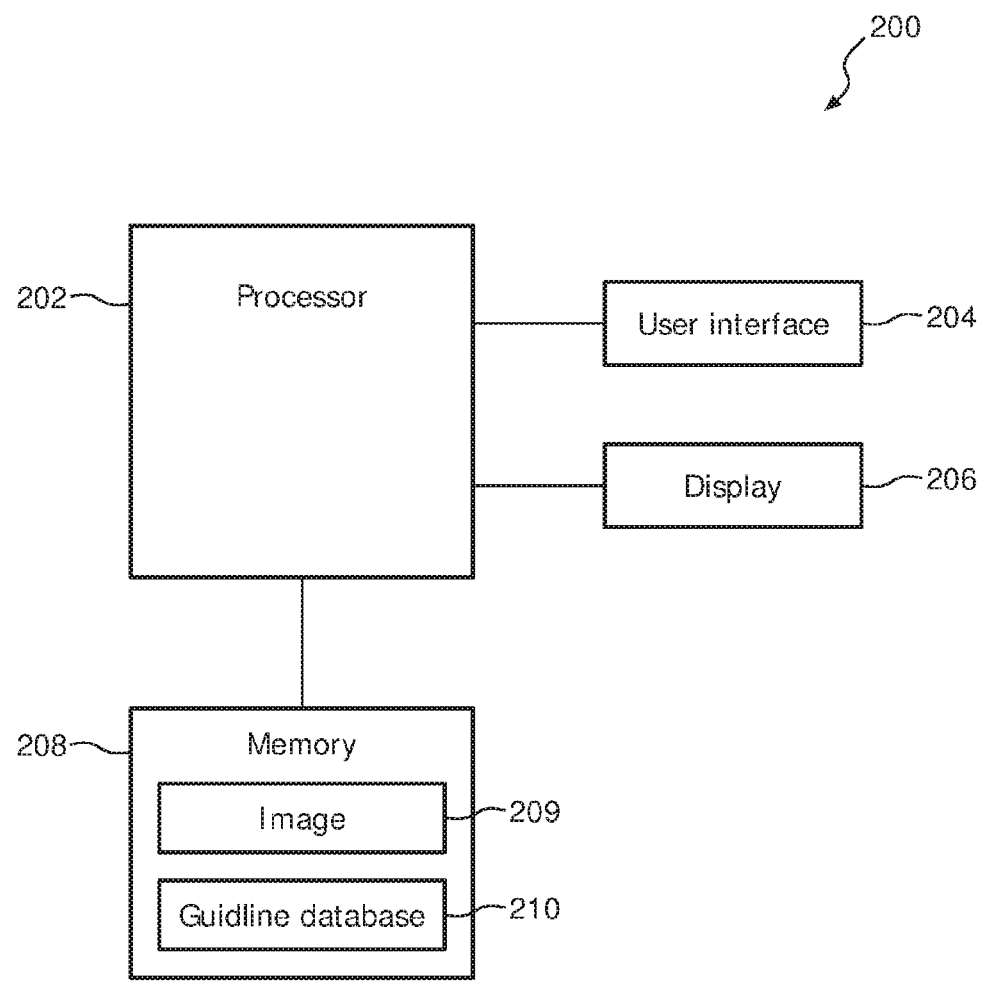
FIG. 2 is a block diagram of an exemplary system according to an exemplary embodiment.

FIG. 2 shows a system 200 according to an exemplary embodiment of the present disclosure on which the exemplary methods of the present disclosure, including the method 100, may be implemented. As shown in FIG. 2, the system 200 includes a processor 202, a user interface 204, a display 206, and a memory 208. The system 200 may illustrate at least a portion of any system a user (e.g., radiologist) may use to read an image. According to certain exemplary embodiments, a radiologist may use the user interface 204 to access an image 209 stored in the memory 208 of the system 200. The system 200 may display the accessed image 209 on the display 206. As described above with respect to step 120, the processor 202 may determine guideline recommendations based on image characteristics of the image being read by the radiologist on the system 200. According to an exemplary embodiment, this action may be performed automatically in response to manual manipulation of the image. For example, using the user interface 204, the radiologist may take a measurement of a nodule or lesion displayed in the image 209, and identify it as a lung nodule. As described herein, this action may trigger the processor 202 to automatically determine recommendations based on the determined image characteristics and accepted guideline(s).

According to an exemplary embodiment, the memory 208 may store a guidelines database 210 and the processor 202 may compare the certain image characteristics to characteristics stored in the guidelines database 210 to determine the corresponding guideline recommendations. Alternatively, the guidelines database 210 may be stored at a remote location and may be accessed by the processor 202 via a network. After the processor 202 determines the corresponding guideline determinations, the guideline determinations may be displayed on the display 206. As described above with respect to the exemplary method 100, Fleischner Guidelines for a low-risk patient and a high-risk patient may be displayed. After the system 200 optionally receives a radiologist's input via the user interface 204, the processor 202 generates a recommendation, and optionally displays the recommendation on the display 206. As described above in regard to the method 100, this recommendation may be included in, for example, a standard radiology report. Alternatively, the recommendation or report may be printed, or transmitted to a remote system. It will be understood by those of skill in the art that the memory 208 may be any computer-readable storage medium, and that the user interface 204 may include any input devices such as, for example, a keyboard, a mouse, a microphone and dictation system, and/or a touch display on the display 206. It will be also understood by those of skill in the art that the system 200 may be a personal computer, a server, or any other known processing arrangement.

Figure 3:
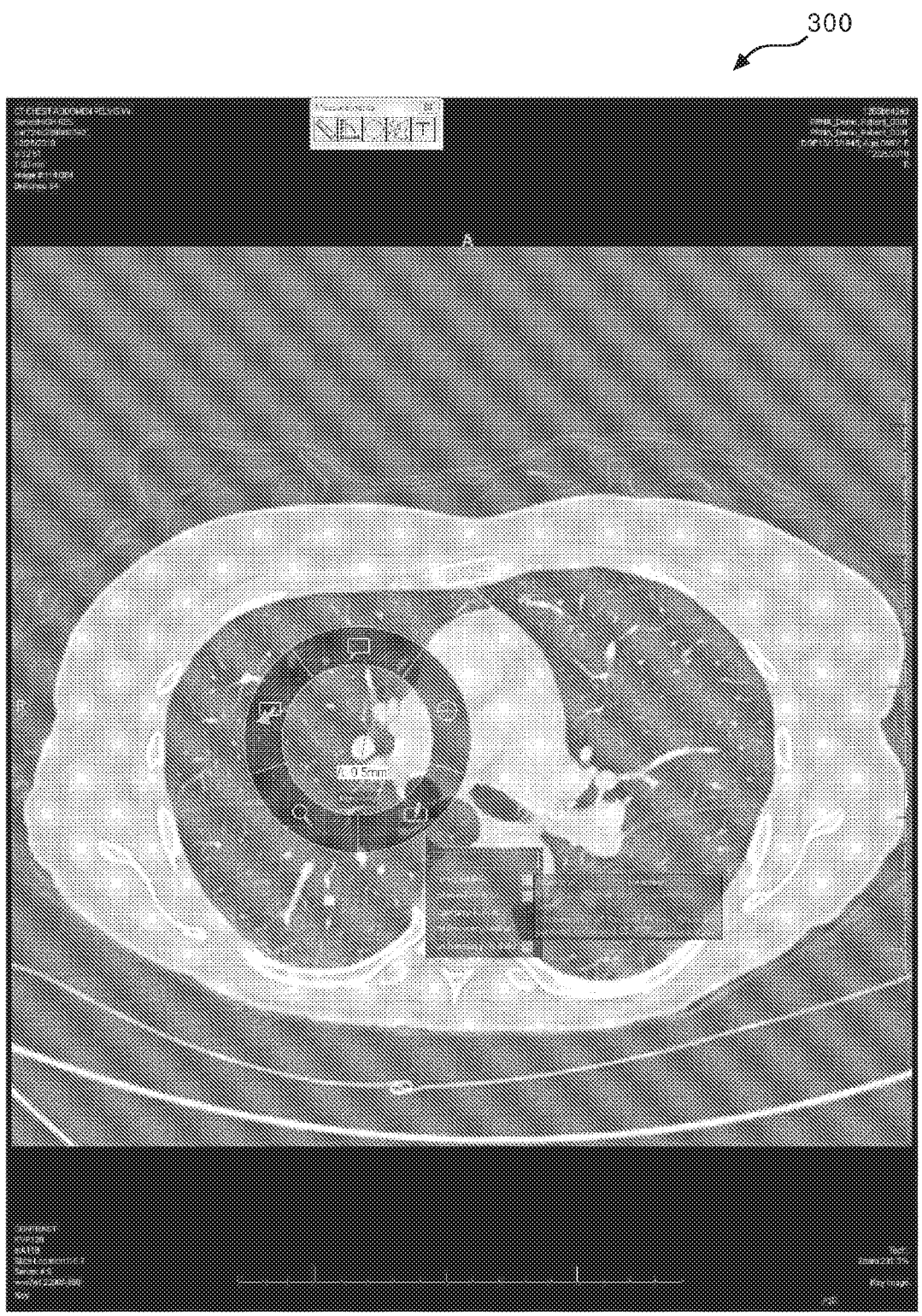
FIG. 3 shows an exemplary screen shot of an image according to an exemplary embodiment.

FIG. 3 shows an exemplary screen shot 300 according to exemplary embodiments of the present disclosure. FIG. 3 shows an exemplary CT image of a 9.5 mm lung nodule. As shown in FIG. 3, the Fleischner guideline recommendations are displayed overlaid on the image. The guideline recommendations may have been automatically determined, for example, in view of the anatomy (i.e., lung) and the size of the nodule (i.e., 9.5 mm). As shown in FIG. 3, the guideline recommendations may be automatically displayed in response to a user interaction via a user interface. For example, as shown in FIG. 3, the guideline recommendations may be automatically displayed after a radiologist has selected 'Lung Nodule' and measured a nodule of interest.

This automated example, using the guidelines, requires that the user provided an indication of the anatomical feature such as 'lung lesion' or 'lung nodule'. In one example system, a graphical user interface may be a ring (e.g., an action wheel including options available to a user), which can be activated by selecting a point on the screen and clicking a specific button. The ring may provide a list of common or likely anatomical parts or findings for this particular type of image scan (e.g., chest CT). Common items marked may include lung/pulmonary/nodules, which are also measured by the radiologist. The user interface (e.g., the ring), enables the user to select anatomy and findings based on the likely anatomy and findings for a given type of exam. For example, a chest CT is likely to include lung, heart, trachea, rib, descending thoracic aorta, vertebral body, but not other regions of the body such as appendix, colon, or humerus. If the image scan does not include any of the list of likely anatomical parts, the anatomy may be listed as unknown. The user interaction (e.g., measurement of the nodule) may trigger the user interface, such as the ring. The ring may include other options in addition to the selection of the anatomy, which may facilitate the radiologist to take an action such as displaying of the recommendations. Other options available via the user interface may include, for example, sending a message, searching, assigning recommendations, etc.

Figure 4:
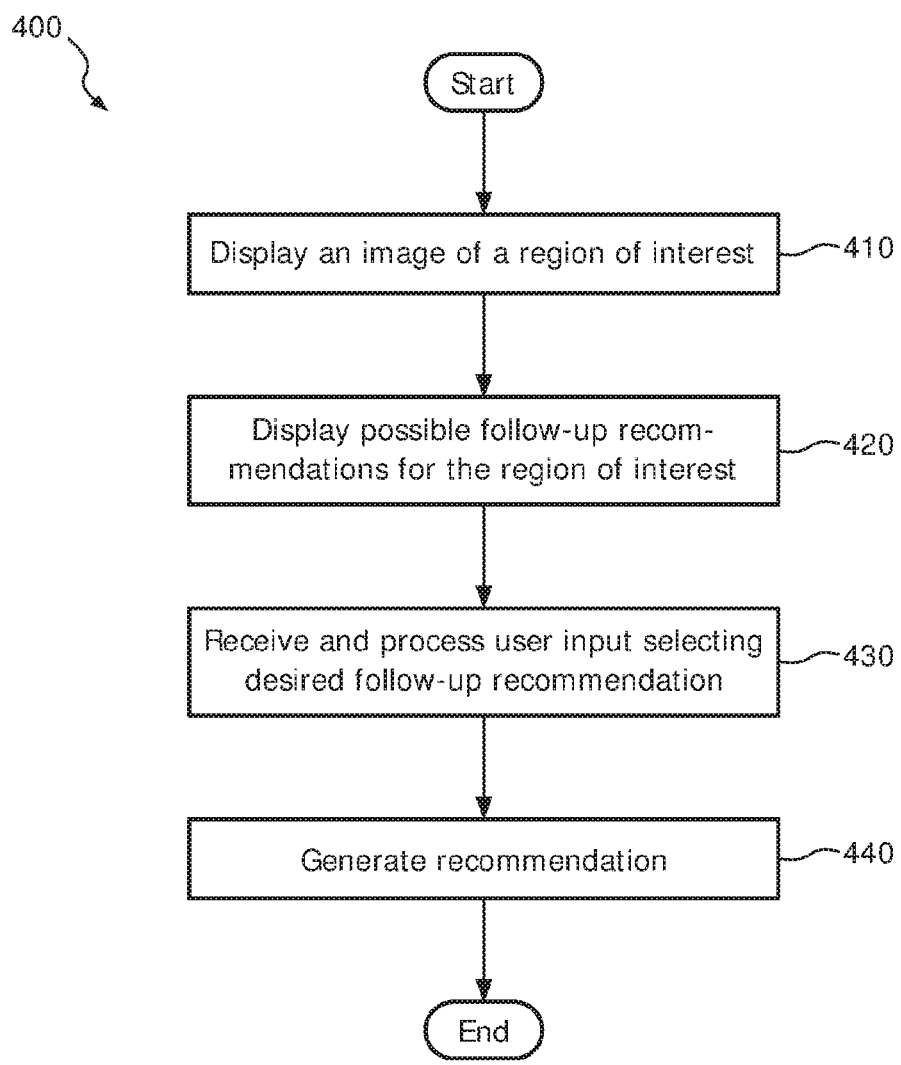
FIG. 4 shows a flow diagram of an exemplary method according to an exemplary embodiment.

FIG. 4 shows an exemplary method 400 according to an exemplary embodiment of the present disclosure. The exemplary method 400 is similar to the exemplary method 100 shown in FIG. 1, however, rather than automatically generating guideline recommendations, the method 400 generates a recommendation based on user input received. Similar to the method 100, an image of of an anatomy of a patient to be read by a user (e.g., a radiologist) is displayed in a step 410. In a step 420, a plurality of possible follow-up recommendations may be displayed to the user. For example, a plurality of possible follow-up modalities (e.g., MRI, CT, Ultrasound, X-Ray) and timeframes (e.g., as soon as possible, within 2 weeks, within 3 months, within 6 months) may be displayed to the user. One or more modalities may be selected from the displayed choices. Further, the lower bound (e.g., 3 months) and upper bound (e.g., 6 months) of a timeframe may be selected to indicate a time period during which the follow up should occur. The possible follow-up recommendations may be displayed via, for example, a pop-up or menu overlaid onto the image. It will be understood by those of skill in the art that display of the possible follow-up recommendations may be prompted by the user. In one embodiment, the user may select an assign recommendation option from a user interface such as, for example, the action wheel shown and described with respect to FIG. 3. The user may then select one or more of the displayed modalities and a displayed timeframe by selecting the desired modality and timeframe from the displayed pop-up or menu. The user's selections for the follow-up recommendations may be based on image characteristics (e.g., anatomy, measurements) of a nodule or tumor of the region of interest determined either automatically or manually via the radiologist.

Alternatively, the system 200 may include a dictation system with defined dictation macros, and the radiologist may dictate a recommended follow-up. According to a first example using instructional macros, a macro may be generated that says: 'Macro CT-Follow-up' where the text generated states: "A CT follow-up is recommended in the timeframe." The radiologist is reminded to enter the timeframe, whereupon he may say: "3 to 6 months." According to another example, the voice macro may be: 'Macro CT6' or 'Macro CT3 to6.' The respective text would state: "A CT follow-up is recommended in 6 months" or "A CT follow-up is recommended in 3 to 6 months." In another example, the voice macro may also embed the recommendation based on the findings such as: 'Macro LungNOdule7 millimeter.' The respective text may state: The Fleischner Guidelines indicates a follow-up CT scan should be performed within 6-12 months in a non-smoker, or in 3-6 months if the patient is a smoker (high risk)."

In a step 430, the processor 202 receives the user input and processes the user input to generate a recommendation, which may be included into a report (e.g., radiology report), in a step 440. As described above in regard to the method 100, the recommendation report may take any of a variety of forms and may be transmitted electronically, or may be printed, or displayed. It will be understood by those of skill in the art, that although the exemplary embodiments describe the recommendation as being included in a standard radiology report, it is not a requirement of this disclosure.

Those skilled in the art will understand that the above-described exemplary embodiments may be implemented in any number of manners, including, as a separate software module, as a combination of hardware and software, etc.

It will be apparent to those skilled in the art that various modifications may be made to the disclosed exemplary embodiment and methods and alternatives without departing from the spirit or scope of the disclosure. Thus, it is intended that the present disclosure covers the modifications and variations provided that they come within the scope of the appended claims and their equivalents.

What is claimed is:

1. A method for generating a radiological report, comprising:

displaying, on a display, a digital radiograph image of a region of interest;

receiving a user input, via a graphical user interface, designating a radiology image characteristic of the region of interest on the display displaying the digital radiograph image, wherein the radiology image characteristic includes an anatomy, wherein the graphical user interface comprises a ring activated by selecting a point on the display and clicking a specific button;

performing, by a processor, a measurement comprising a three-dimensional (3D) volume of the anatomy, wherein the processor performs the measurement using image processing techniques;

determining, by the processor, a radiological recommendation based on the user input, the measurement, and a Fleischner Guideline risk factor;

displaying the radiological recommendation overlaid on the digital radiograph image, wherein the displaying of the radiological recommendation is automatically overlaid on the digital radiograph image in relation to the radiology image characteristic such that the overlaid radiological recommendation does not cover the radiology image characteristic, and wherein the determining and displaying the radiological recommendation is automatically triggered when the user input is received;

receiving further user input comprising a modification of the radiological recommendation; and generating, by the processor, a report including the modified radiological recommendation.

2. The method of claim 1, wherein the radiological recommendation includes a modality.

3. The method of claim 1, wherein determining the radiological recommendation includes:

comparing via the processor, the anatomy and the measurement to a corresponding anatomy and a corresponding measurement stored in a guidelines database; and determining, via a processor, a corresponding guideline recommendation associated with the anatomy and the measurement as the recommendation.

4. The method of claim 1, further comprising displaying a plurality of possible radiological recommendations.

5. The method of claim 1, wherein determining the radiological recommendation includes receiving a user input selecting the radiological recommendation.

6. The method of claim 5, wherein the user input includes voice input.

7. The method of claim 1, further comprising displaying the report including the radiological recommendation on a radiology system.

8. The method of claim 1, further comprising changing a display of the digital radiograph image of the region of interest to show a user interface including available options, one of the available options including displaying the radiological recommendation.

9. A radiology system for generating a radiological report, comprising:

a display configured to display a digital radiograph image including a region of interest;

a graphical user interface configured to receive a user input designating a radiology image characteristic of the region of interest on the display displaying the digital radiograph image, wherein the radiology image characteristic includes an anatomy, wherein the graphical user interface comprises a ring activated by selecting a point on the display and clicking a specific button; and a processor configured to perform a measurement comprising a three-dimensional (3D) volume of the anatomy using image processing techniques, determine a radiological recommendation based on the radiology image characteristic, the measurement, and a Fleischner Guideline risk factor, display the radiological recommendation overlaid on the image and generate a report including the radiological recommendation, wherein the displaying of the radiological recommendation is automatically overlaid on the image in relation to the radiology image characteristic such that the overlaid radiological recommendation does not cover the radiology image characteristic, wherein the determining and displaying the radiological recommendation is automatically triggered when the user input is received, and modify the radiological recommendation based on further user input.

10. The system of claim 9, wherein the radiological recommendation includes a modality and a timeframe.

11. The system of claim 9, wherein the processor determines the radiological recommendation based on the anatomy and the measurement by comparing the anatomy and the measurement to a corresponding anatomy and a corresponding measurement stored in a guidelines database and determines a corresponding guideline recommendation associated with the anatomy and the measurement as the recommendation.

12. The system of claim 9, wherein the system displays a plurality of possible radiological recommendations.

13. The system of claim 9, wherein the user input includes voice input.

14. The system of claim 9, wherein the display displays the report including the radiological recommendation on the radiology system to a radiologist.

15. The system of claim 9, wherein the processor changes a display of the digital radiograph image of the region of interest to show a user interface including available options, one of the available options including displaying the radiological recommendation.

16. The method of claim 1, wherein the radiological recommendation comprises an audio file.

17. The method of claim 1, wherein the radiological recommendation is a follow up radiology procedure to occur within 3-12 months.

18. The method of claim 1, wherein the Fleischner Guideline risk factor is nodule size and location.

19. The method of claim 1, wherein the Fleischner Guideline risk factor is prevalence of granulomatous infections in a geographic area of the patient.

20. The system of claim 9, wherein a radiological follow up recommendation pop-up or menu is overlaid on the displayed digital radiograph image.

21. The system of claim 9, wherein the radiological system for generating a radiological report is a Picture Archive and Communications System used by a radiologist for reading an image or set of images and reporting findings.

22. A non-transitory medium comprising computer-readable instructions executable for:

displaying, on a display, a digital radiograph image of a region of interest;

receiving a user input, via a graphical user interface, designating a radiology image characteristic of the region of interest on the display displaying the digital radiograph image, wherein the radiology image characteristic includes an anatomy, wherein the graphical user interface comprises a ring activated by selecting a point on the display and clicking a specific button;

performing, by a processor, a measurement comprising a three-dimensional (3D) volume of the anatomy, wherein the processor performs the measurement using image processing techniques;

determining, by the processor, a radiological recommendation based on the user input, the measurement, and a Fleischner Guideline risk factor;

displaying the radiological recommendation overlaid on the digital radiograph image, wherein the displaying of the radiological recommendation is automatically overlaid on the digital radiograph image in relation to the radiology image characteristic such that the overlaid radiological recommendation does not cover the radiology image characteristic, and wherein the determining and displaying the radiological recommendation is automatically triggered when the user input is received;

receiving further user input comprising a modification of the radiological recommendation; and generating, by the processor, a report including the modified radiological recommendation.

\* \* \* \* \*